(12) United States Patent
Wachtel et al.

(10) Patent No.: US 8,511,300 B2
(45) Date of Patent: Aug. 20, 2013

(54) INHALER

(75) Inventors: Herbert Wachtel, Ingelheim am Rhein (DE); Quentin John Harmer, Cambridge (GB); Stephen William Eason, Cambridge (GB)

(73) Assignee: Vectura Delivery Devices Limited, Chippenham (GB)

( * ) Notice: Subject to any disclaimer, the term of this patent is extended or adjusted under 35 U.S.C. 154(b) by 282 days.

(21) Appl. No.: 12/864,386

(22) PCT Filed: Jan. 19, 2009

(86) PCT No.: PCT/EP2009/000293
§ 371 (c)(1),
(2), (4) Date: Nov. 15, 2010

(87) PCT Pub. No.: WO2009/092550
PCT Pub. Date: Jul. 30, 2009

(65) Prior Publication Data
US 2011/0041841 A1    Feb. 24, 2011

(30) Foreign Application Priority Data
Jan. 24, 2008  (EP) .................................. 08001296

(51) Int. Cl.
*A61M 15/00* (2006.01)
*A61M 11/00* (2006.01)
(52) U.S. Cl.
USPC ................................ 128/200.21; 128/203.21
(58) Field of Classification Search
USPC ............. 128/203.12, 203.15, 203.19, 203.21, 128/203.23, 203.24, 203.25
See application file for complete search history.

(56) References Cited

U.S. PATENT DOCUMENTS

| 5,724,960 | A | * | 3/1998 | Bruna | 128/203.15 |
|---|---|---|---|---|---|
| 6,116,237 | A | | 9/2000 | Schultz | |
| 6,182,655 | B1 | * | 2/2001 | Keller et al. | 128/203.15 |
| 6,948,494 | B1 | * | 9/2005 | Snow | 128/203.15 |
| 2002/0170560 | A1 | | 11/2002 | Young et al. | |
| 2004/0163644 | A1 | | 8/2004 | Gieschen et al. | |
| 2007/0062519 | A1 | * | 3/2007 | Wuttke et al. | 128/200.14 |
| 2007/0137645 | A1 | * | 6/2007 | Eason et al. | 128/203.15 |
| 2010/0139654 | A1 | * | 6/2010 | Thoemmes et al. | 128/203.15 |
| 2011/0132358 | A1 | | 6/2011 | Eason et al. | |

FOREIGN PATENT DOCUMENTS

| GB | 2407042 A | 4/2005 |
|---|---|---|
| JP | 1998508790 | 9/1998 |
| JP | 2007533363 | 11/2007 |
| WO | WO 9609085 A1 | 3/1996 |

(Continued)

OTHER PUBLICATIONS

Search Report from the European Patent Office, dated Mar. 31, 2009, issued in connection with corresponding EP Application No. 2082773 A1.

(Continued)

*Primary Examiner* — Loan Thanh
*Assistant Examiner* — Andrew S Lo
(74) *Attorney, Agent, or Firm* — Davidson, Davidson & Kappel, LLC

(57) ABSTRACT

A passive inhaler for delivery of a powder-form inhalation formulation from a blister strip with a plurality of blister pockets is proposed. The inhaler has a flow resistance of at least 75000 $Pa^{1/2}s/m^3$.

4 Claims, 4 Drawing Sheets

(56) References Cited

FOREIGN PATENT DOCUMENTS

| WO | WO 97/25086 A | 7/1997 |
| WO | WO 00/21594 A | 4/2000 |
| WO | WO 03/084502 A | 10/2003 |
| WO | WO 2007096111 A2 * | 8/2007 |

OTHER PUBLICATIONS

Office Action dated Mar. 19, 2013, from the Japanese Patent Office concerning the corresponding Japanese Application No. 2010-543421.

* cited by examiner

INHALER

This application is a U.S. national phase application under U.S.C. §371 of International Application No. PCT/EP2009/000293, filed Jan. 19, 2009, which claims priority to European Patent Application No. EP08001296.6, filed Jan. 24, 2008, the disclosures of which are hereby incorporated by reference in their entirety.

FIELD OF THE INVENTION

The present invention relates to an inhaler according to the preamble of claim 1 or 6.

The present invention relates to an inhaler for delivery of a powder-form inhalation formulation from a blister strip with a plurality of blister pockets (also called blisters) containing the inhalation formulation in doses.

BACKGROUND OF THE INVENTION

GB 2 407 042 A discloses an inhaler with a rolled-up blister strip. The inhaler comprises a manually operated, pivotable actuator, which operates a conveyor for stepwise moving the blister strip. The actuator supports a piercer and an associated mouthpiece. By pivoting the actuator, the blister strip and be moved forward and blister pockets of the blister strip can be pierced one after the other. When a patient breathes in an air stream passes through the previously pierced blister pocket, with the result that the inhalation formulation in the blister pocket mixes with the air and is discharged to the patient.

SUMMARY OF THE INVENTION

The present invention relates to passive inhalers, i.e. inhalers where the patient or user breathes in to generate an air stream, which entrains the inhalation formulation and forms the desired aerosol.

When a patient puts a mouthpiece or any other end piece in his mouth and breathes in, an air stream is sucked through the inhaler to generate the aerosol and to discharge the inhalation formulation as aerosol. A pressure drop occurs within the inhaler when the air stream flows through the inhaler. This pressure drop depends on the flow per time and flow velocity. The flow resistance represents a quantity relating to the square root of the pressure drop at a certain flow rate. In the present invention, the term "flow resistance" means the resistance which occurs when air is sucked from the mouthpiece or any other end piece of the inhaler during inhalation, i.e. with generation of an aerosol of the inhalation formulation.

In contrast to active inhalers, where an active means such as a propellant, a pump, an air pump or any other pressure generator or compressed or liquefied gas, generates the aerosol, passive inhalers usually have a higher flow resistance for the patient or user. This results from the fact that the generation of aerosol requires energy and, thus, leads to a respective flow resistance in passive inhalers. Nevertheless, it has been an object of the previous developments to keep the flow resistance as low as possible in both types of inhalers in order to facilitate inhalation for the patient or user.

Object of the present invention is to provide an inhaler with optimized discharge characteristics.

The above object is achieved by an inhaler according to claim 1 or 6. Advantageous embodiments are subject of the subclaims.

One aspect of the present invention is that the flow resistance of the inhaler is increased. In particular, the inhaler has a flow resistance of at least 75000 $Pa^{1/2}s/m^3$. This is significantly higher than previous inhalers of the present type. Such inhalers usually have a flow resistance of only about 60000 $Pa^{1/2}s/m^3$.

The increased flow resistance results in optimized discharged characteristics of the inhaler. Due to the higher flow resistance the patient or user will breath in more slowly so that the total inhalation time is increased. In particular, the higher flow resistance takes it easier for the patient or user to slowly breath in. This applies to intuitive breathing as well as to willful breathing. Thus, a lower flow velocity can be achieved in the mouth and pharynx region, which results in lower impaction of the aerosol particles (inhalation formulation) in this region so that the percentage of lung deposition of the inhalation formulation is increased.

Another aspect of the present invention is that the mouthpiece comprises an insert to increase the flow resistance. This allows a very simple construction and in particular to adapt the flow resistance as desired in previous constructions in a very easy and cost-effective manner.

A further aspect of the present invention is that the smallest cross sectional area of the feeding path of air limits the feeding air stream and/or is smaller than the blister opening. So it is possible to ensure defined flow characteristics and, in particular, to avoid the influence of differing opening sizes in the punctured lid of an opened blister pocket.

Another aspect of the present invention is that the smallest cross sectional area of a bypass path of the air stream is smaller than the smallest cross sectional area of the feeding path. The bypass path bypasses the blister pocket. The feeding path is connected to the blister pocket. Thus, it is possible to ensure a high flow velocity through the blister pocket to entrain the inhalation formulation, to deagglomerate the inhalation formulation and to generate the aerosol in a very effective manner.

Still a further aspect of the present invention is that the mean (flow) velocity is at least 50 m/s at a total flow volume of 39 l/min in the mixing zone of the feeding path and bypass path or at the end of the feeding path. This ensures good deagglomeration and generation of a aerosol with the desired flow characteristics.

BRIEF DESCRIPTION OF DRAWINGS

Further aspects, features, properties and advantages of the present invention are described in the claims and the subsequent description of a preferred embodiment, with reference to the drawing. There are shown in:

In the Figures, the same reference numbers are used for identical or similar parts, even if a repeated description is omitted. In particular identical or corresponding advantages and properties then also result or may be achieved.

DETAILED DESCRIPTION OF THE INVENTION

Figure 1:
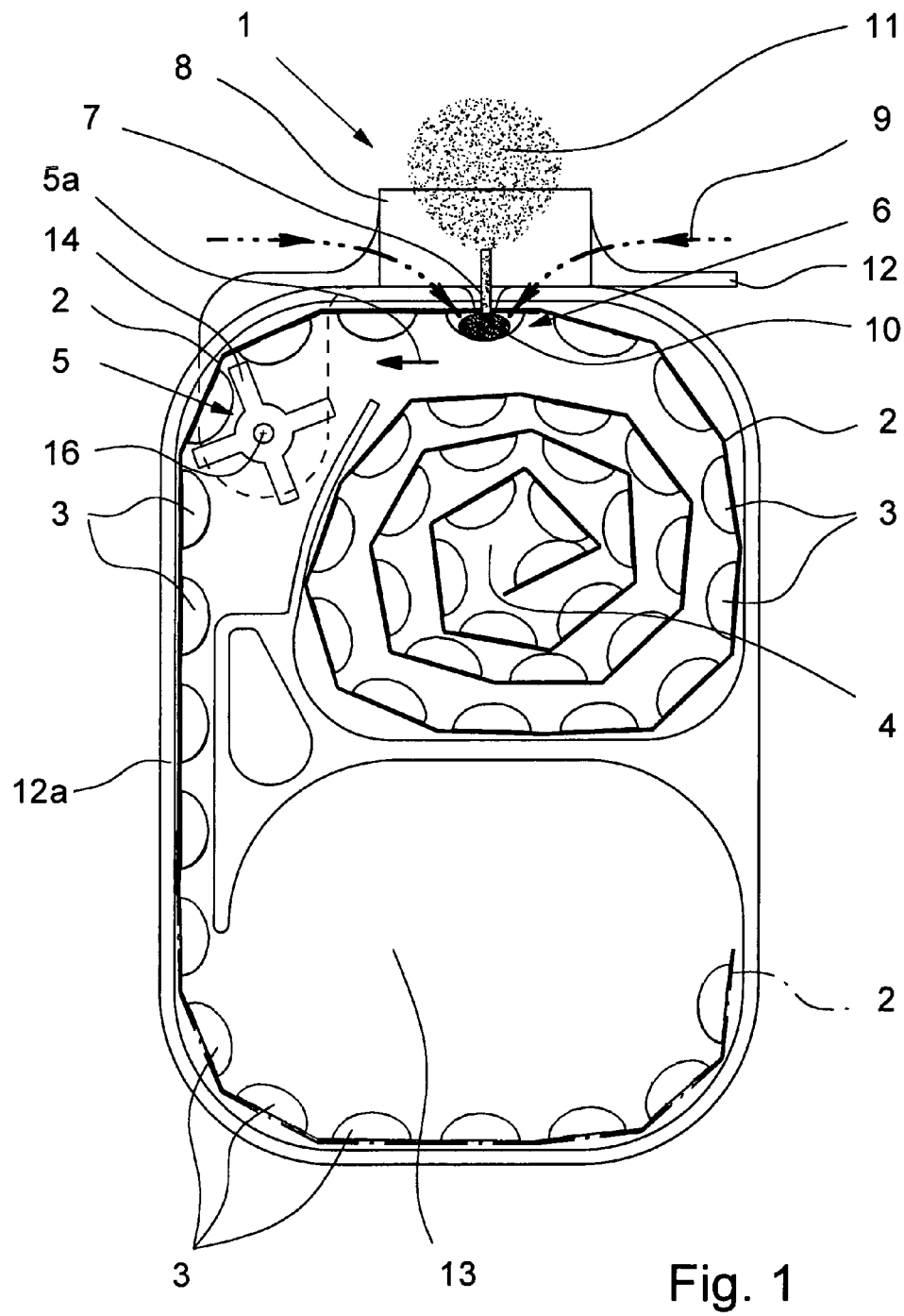
FIG. 1 a schematic sectional view of an inhaler without mouthpiece cover.

FIG. 1 shows in a schematic sectional representation an inhaler 1.

The inhaler 1 serves to deliver a powdered inhalation formulation from a band-shaped blister strip 2. The blister strip 2 is finite, not forming an endless or closed loop. It has a large number of blister pockets 3 respectively containing directly a dose of the loose inhalation formulation. Thus, the formulation is pre-metered.

The inhaler 1 has a reservoir 4 for the still unused blister strip 2 with closed (sealed) blister pockets 3. The blister strip 3 is rolled up or wound up in the reservoir 4. In the representation example the reservoir 4 is formed such that the blister strip 2 can be moved outwards or pulled out of the reservoir 4 as easily as possible.

In the representation example the blister strip 2 is directly received in the reservoir 4. However, instead of this a cassette, a container, a drum or suchlike can also be fitted or inserted with the blister strip 2 into the inhaler 1 or the reservoir 4.

The inhaler 1 has a conveyor 5 for stepwise onward movement of the blister strip 2 in direction of arrow 5a by one blister pocket 3 in each case, in order to feed the blister pockets 3 successively to an opening and/or removal position 6 where the respective blister pocket 3 is opened and can be emptied.

The blister pockets 3 can be opened respectively preferably by means of a piercing member 7 which punctures or cuts open a lid of the respectively aligned blister pocket 3 in position 6. The piercing member 7 is hollow and in fluid connection with an adjacent mouthpiece 8 of the inhaler 1.

During or for inhalation a patient or user, not represented, places the mouthpiece 8 in his mouth and breathes in. The respectively opened blister pocket 3, into which the piercing member 7 extends, is thereby emptied by sucking in. An air stream 9 of ambient air is sucked in and passed through the opened blister pocket 3 such that the loose powder 10 (forming the inhalation formulation and being schematically shown in FIG. 1 only in the actually opened blister pocket 3 below mouthpiece 8) is dispensed with the sucked-in ambient air as an aerosol cloud 11 via the mouthpiece 8. This situation is schematically represented in FIG. 1.

The inhaler 1 has a preferably manually actuatable, lever-like actuator 12 being pivotally mounted to a housing 12a of the inhaler 1. The piercing member 7 and the mouthpiece 8 are attached to and supported by the actuator 12.

The actuator 12 is operable (pivotable) to cause the piercing member 7 to puncture the lid of the respectively aligned blister pocket 3 in position 6 below the mouthpiece 8.

Figure 3:
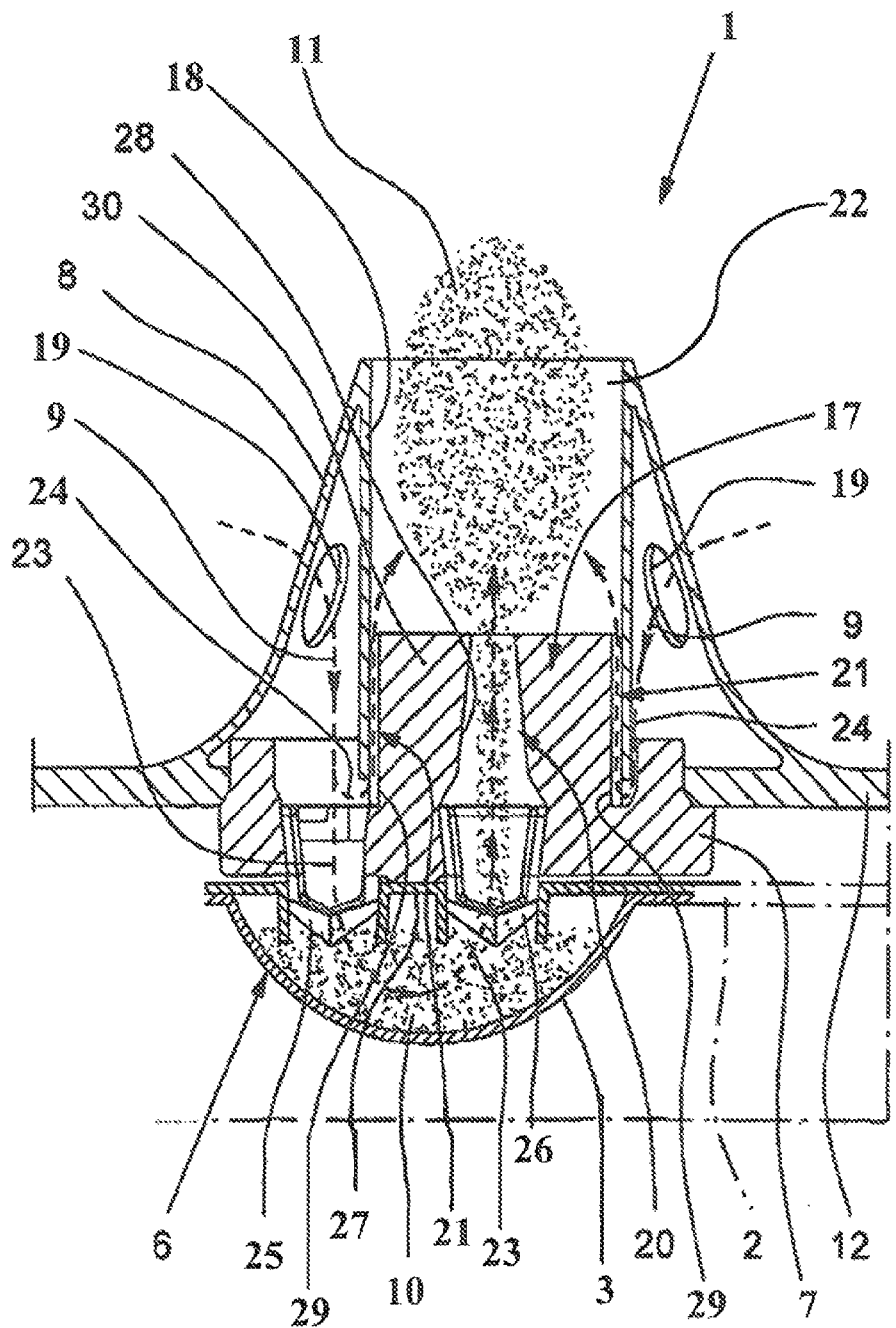
FIG. 3 an enlarged sectional view of the inhaler in the region of a mouthpiece and a piercing member.

When the actuator 12 swivels from the position shown in FIG. 1 (here anti-clockwise) to the partially opened position shown in FIG. 3, the piercing member 7 is withdrawn from the last-pierced blister pocket 3.

Then, the blister strip 2 is moved forward by one blister pocket 3, so that the next blister pocket 3 is moved in position 6. This will be explained in more detail later.

When the actuator 12 swivels back into the position shown in FIG. 1, i.e. is manually moved back, the next aligned blister pocket 3 of the blister strip 2 is punctured by the piercing member 7 and thereby opened. Then, the next inhalation can take place, i.e. the inhaler 1 is activated.

The inhaler 1 has a receiving space or apparatus 13 to receive or store the used part of the blister strip 2. The receiving space or apparatus 13 is formed such that the used part can be wound up. FIG. 1 shows a situation with essentially filled reservoir 4 and still essentially empty receiving space 13.

The conveyor 5 comprises a conveying wheel 14, which can engage between the blister pockets 3 and thus convey the blister strip 2 in form-locking or form-fit manner. This allows very secure or precise moving or indexing of the blister strip 2 as desired and/or necessary.

The conveyor 5 or its conveying wheel 14 is arranged between the reservoir 4 and the receiving apparatus 13, in particular between the removal position 6 and the receiving apparatus 13, thus after the emptying of the blister pockets 3.

The pivot axis of the actuator or lever 12 is coaxial with the rotation axis of the conveying wheel 14. In particular, the actuator or lever 12 may be supported by an axle of the conveying wheel 14.

Figure 2:
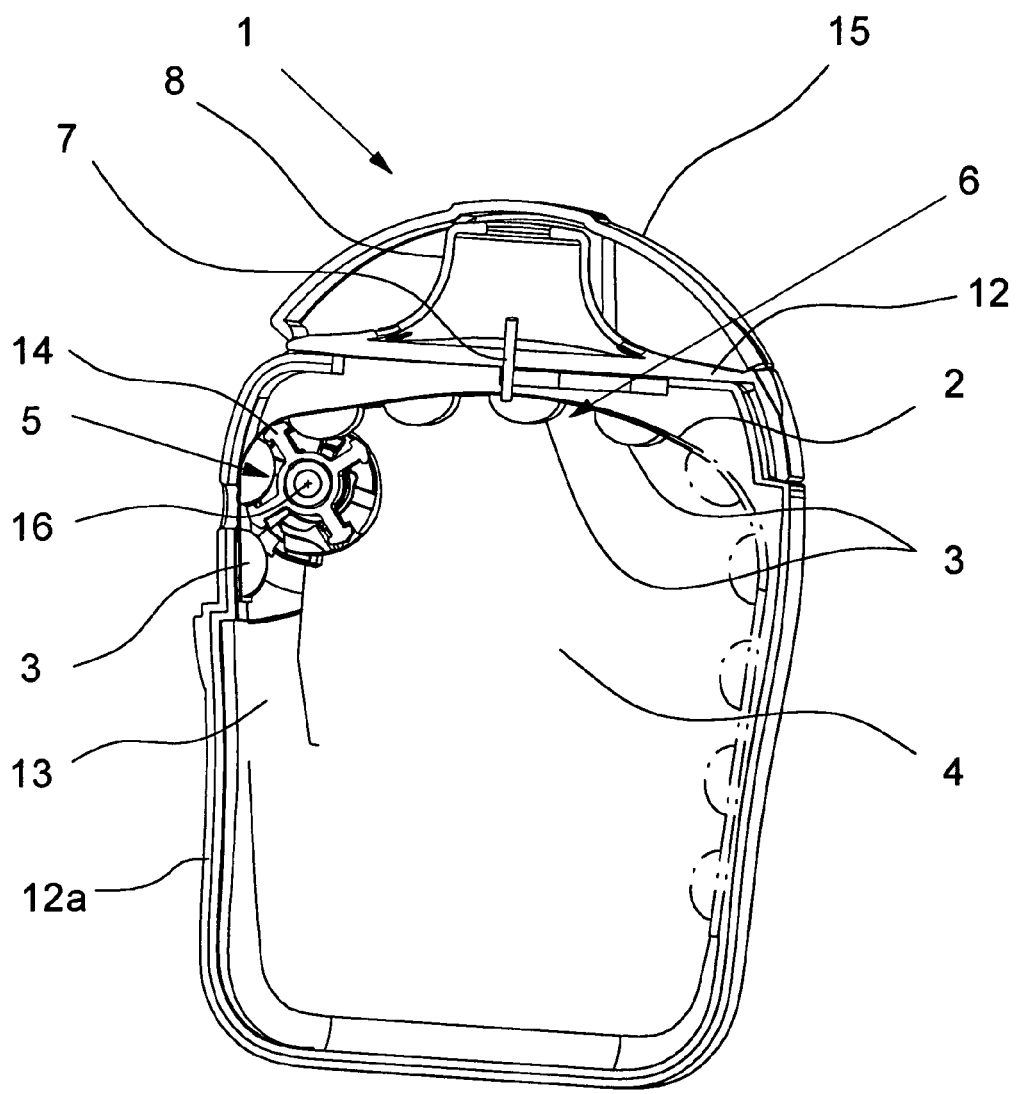
FIG. 2 a schematic sectional representation of the inhaler with closed mouthpiece cover.

The inhaler 1 comprises a mouthpiece cover 15. The mouthpiece cover 15 is not shown in FIG. 1 which explains only the basic principle of the inhaler 1, but in FIG. 2 which shows a more realistic, but still schematic sectional view of the inhaler 1. FIG. 2 shows the inhaler 1 with closed mouthpiece cover 15, wherein the blister strip 2 has been partly omitted for illustration purposes. FIG. 3 shows the inhaler 1 with completely opened mouthpiece cover 15.

The mouthpiece cover 15 is pivotable around a cover axis 16 which is indicated in FIGS. 2 and 3 and extends perpendicular to the drawing plane in the present representation.

The pivot axis of the actuator 12 extends coaxial to or with the cover axis 16. The rotation axis of the conveying wheel 14 extends coaxial to the cover axis 16 and to pivot axis of the actuator 12.

The conveyor 5 or its conveying wheel 14 is driven by the mouthpiece cover 15, namely by the pivotal movement of the mouthpiece cover 15. In particular, the blister strip 2 is moved forward, when the mouthpiece cover 15 is opened. Preferably, only part of the opening movement of the mouthpiece cover 15 actuates or operates the conveyor 5 or its conveying wheel 14 to move the blister strip 2 forward.

When the mouthpiece cover 15 is opened starting with the completely closed position shown in FIG. 2, in a first phase of the opening movement, for example up to a first angle of about 10, 20 or 30 degrees, the blister strip 2 is not moved due to a respective freewheel (not shown) between the mouthpiece cover 15 and the conveying wheel 14.

First of all, the actuator 12 has to be moved or opened in order to withdraw the piercing member 7 from the previously pierced and usually/already emptied blister pocket 3. This opening movement of the actuator can be performed manually. However, the actuator 12 preferably opens automatically when opening the mouthpiece cover 15. In particular, the mouthpiece cover 15 can be opened up to the first angle. When the mouthpiece cover 15 reaches this angle, e.g. about 20 degrees, the actuator 12 flips automatically open into its opened position shown in FIG. 2, in particular due to a biasing or spring means (not shown) or the like. However, it also possible that the actuator 12 moves jointly with the mouthpiece cover 15 in the first phase of the opening movement (e.g. due to a ratchet mechanism, spring or the like) until the actuator 12 reaches its opened position or the first angle.

The opened position of the actuator 12 is preferably set such that the piercing member 7 is not exposed to the exterior and/or that the inhaler 1 is not completely opened in order to avoid or at least minimize any potential external influences.

In order to limit the open position of the actuator 12, the opening or pivot range of the actuator 12 is smaller than the one of the mouthpiece cover 15 and/or is restricted to preferably at most 20 degrees, in particular to about 10 degrees or less.

However, it is also possible that the actuator 12 is not limited in its opening position, but can open or pivot as far as the mouthpiece cover 15, in particular jointly with the mouthpiece cover 15.

During the further opening (second phase) of the mouthpiece cover 15, the conveyor 5 or its conveying wheel 14 is actuated to move or index the blister strip 2 by one blister pocket 3 onward to the next blister pocket 3 that shall be emptied. This blister movement happens preferably up to the complete opening of the mouthpiece cover 15.

Only when the mouthpiece cover 15 is opened completely, i.e. reaches its end position, the movement of the blister strip 2 is set or fixed by a respective mechanism (not shown) and/or decoupled from the mouthpiece cover movement to keep the next blister pocket 3 in position 6 for puncturing. However, if the mouthpiece cover 15 is not fully opened and closed again, then, the blister strip 2 is moved backward. This facilitates operation of the inhaler 1 and, in particular, prohibits that incomplete or unintended operation of the mouthpiece cover 15 results in an undesired movement of the blister strip 2 and eventually in an undesired opening of the next blister pocket 3.

Preferably, a lock (not shown) is provided so that the opened actuator 12 can be closed again only if the mouthpiece cover 15 has been fully opened or has been pivoted back to the first angle or the last-pierced blister pocket 3 has been moved back into position 6. Thus, the piercing member 7 cannot be pushed against an area of the blister strip 2 without or beside a blister pocket 3.

When the mouthpiece cover 15 has been fully opened and the next blister pocket 3 has been moved in position 6, the actuator 12 can be pivoted back, i.e. closed, in order to pierce the already aligned, still closed blister pocket 3. Then, the inhaler 1 is ready for inhalation, i.e. activated as already described.

After inhalation, the inhaler 1 can be closed by pivoting back the mouthpiece cover 15 into its closed position.

In order to operate the conveyor 5 or its conveying wheel 14 by movement of the mouthpiece cover 15 as described above or in any other suitable manner, the mouthpiece cover 15 is coupled with the conveyor 5, in particular the conveying wheel 14, via the already mentioned freewheel and a suitable transmission, a slipping clutch or any other suitable coupling or the like.

Preferably, the freewheel, transmission, coupling or the like is integrated into or located adjacent to the conveying wheel 14 or a respective axle.

Preferably, the mouthpiece cover 15 covers axially an axle or the axis of the actuator and/or conveying wheel 14.

FIG. 3 shows in an enlarged sectional view the piercing member 7 with the mouthpiece and an opened blister pocket 3 in the removal position 6. It can be seen that the piercing member 7 preferably comprises an insert 17 which is connected to the mouthpiece 8 and, in particular, extends into an outlet space or tube 18 of the mouthpiece 8.

The inhaler 1 or mouthpiece 8 comprises preferably at least one, here multiple air openings 19 through which the air stream 9 of ambient air can flow in.

The piercing member 7 and the mouthpiece 8 and/or the insert 17 form a feeding path 20 for the air which has been flown through the opened blister pocket 3 and, in addition, a bypass path 21 for air bypassing the blister pocket 3. Both paths 20 and 21 end preferably within the mouthpiece 8 or its outlet tube 18 and/or at a mixing zone 22 where the respective streams through the paths 20 and 21 mix.

In particular, the air stream 9 entering through the air openings 19 is split up into a feeding air stream 23 flowing through the opened blister pocket 3 and them through the feeding path 20, and into a bypass air stream 24 flowing through the bypass path 21.

FIG. 3 shows schematically the aerosol generation when the air flows. The feeding air stream 23 flowing through the opened blister pocket 3 entrains the inhalation formulation (powder 10) and flows into the mouthpiece 8 or its outlet tube 18, in particular to the mixing zone 22 where it mixes with the bypass air stream 24. Thus, the aerosol cloud 19 is generated as schematically shown in FIG. 3.

Figure 4:
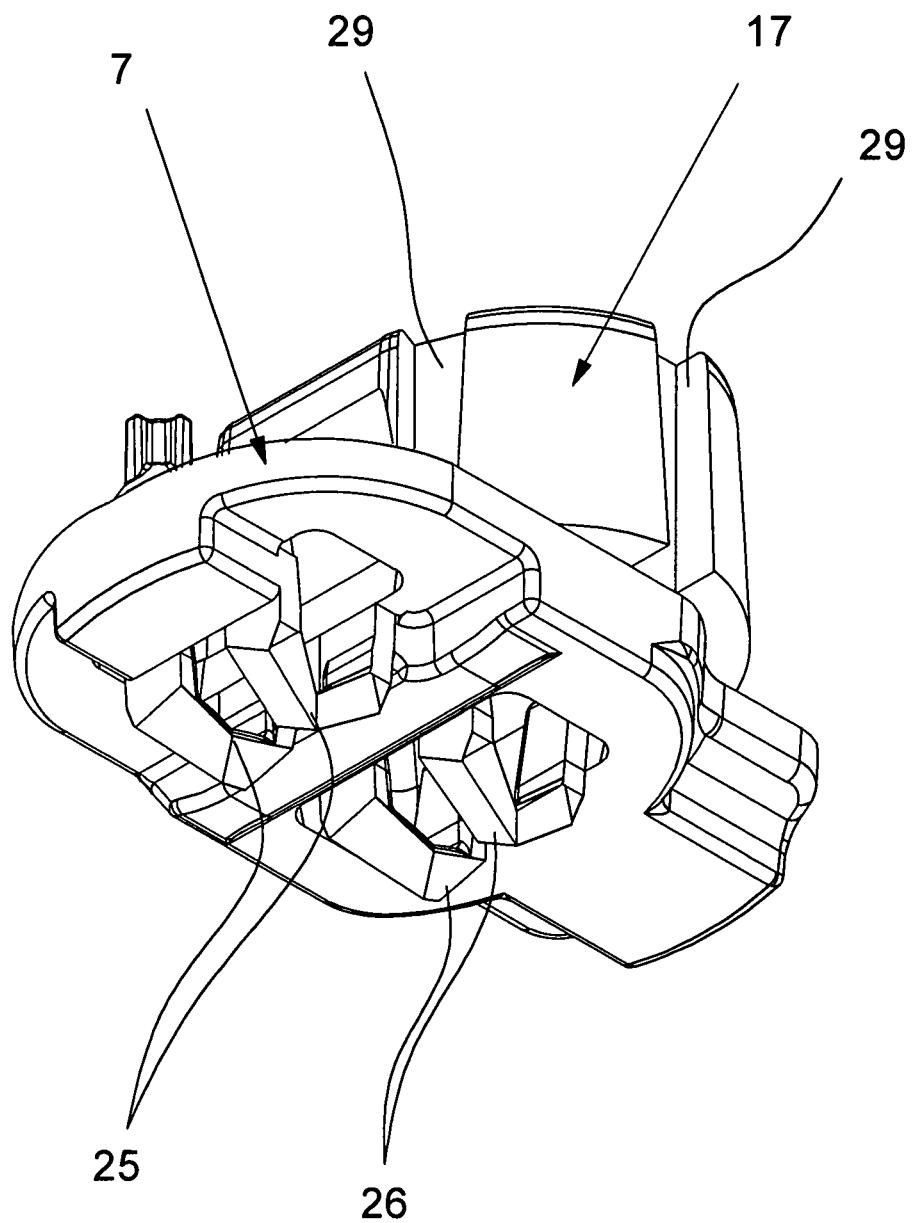
FIG. 4 a perspective view of the piercing member with an insert seen from the piercing side.

In the present embodiment, the piercing member 7 preferably comprises two piercer elements 25 and 26 as shown in FIG. 3 and in the perspective view of the piercing member 7 according to FIG. 4.

The first piercing element 25 serves to form a first blister opening (inlet opening) in the lid 27 of the blister pocket 3 as shown in FIG. 3. The second piercing element 26 forms a separate, second blister opening (outlet opening) in the lid 27 as schematically shown in FIG. 3. Thus, the feeding air stream 23 can flow in through the first opening and out through the second opening. The second opening is fluidically connected to the feeding path 20 within is formed here preferably by a channel 28 within the piercing member 7 and/or insert 17. This channel 28 opens to the mixing zone 22 in the present embodiment.

In the present embodiment, the bypass path 21 leads through or is formed by one, preferably multiple channels or grooves 29, preferably formed by the insert 17, to the mixing zone 22. In particular, the grooves 29 are radically covered by the outlet tube 18 of the mouthpiece 8. However, other constructional solutions are possible.

The insert 17 is located adjacent to the piercing member 7. In particular, the piercing member 7 forms or holds the insert 17 or vice versa.

Preferably, the insert 17 is held form-fit within the mouthpiece 8 or its outlet tube 18. However, other construction solutions are also possible.

The piercing member 7 is connected with the actuator 12 and/or the mouthpiece 8 as shown in FIG. 3. In particular, the piercing member 7 is essentially plate-like with the two piercing elements 25, 26 protruding and extending towards the blister pocket 3 to be opened.

Preferably, the inhaler 1 has a flow resistance of a least 75000 $Pa^{1/2}s/m^3$, in particular of at least 90000 $Pa^{1/2}s/m^3$, more preferably about 96000 $Pa^{1/2}s/m^3$ or more. The flow resistance is preferably defined or set by the piercing member 7 and/or insert 17.

The flow resistance is the quotient of the square root of the pressure drop divided by the flow rate. For example, a pressure drop of 4000 Pa results at a flow rate of 39 l/min in a flow resistance of 97301 $Pa^{1/2}s/m^3$.

Thus, a relatively slow inhalation can be achieved. In particular, the duration of the inhalation can be prolonged and/or a relatively low flow velocity or rate through the mouthpiece 8 or its outlet tube 18 can be achieved, even if the patient or user breaths in only intuitively.

Preferably, the smallest cross sectional area of the feeding path 20 (here of channel 28) limits the feeding air stream 23 and/or is smaller than the blister opening (here smaller than the smaller one of the first and second blister openings). This allows definition or provision of a well defined flow resistance and flow properties. In particular, the flow properties do not depend on the actual size of the blister opening(s) which can very from one blister pocket 3 to the next one.

Preferably, the smallest cross sectional area of the bypass path 21 (here formed by the cross sectional areas of the grooves 29) is smaller than the smallest cross sectional area of the feeding path 20. Thus, the major part of the (total) air stream 9 is guided through the feeding path 20. With other words, the feeding air stream 23 has preferably a larger flow rate than the bypass air stream 24.

In particular, the smallest cross sectional area of the bypass path 21 is at most 80% preferably about 70% or less, of the smallest cross sectional area of the feeding path 20. Thus, the flow rate of the bypass air stream 24 is significantly lower than the flow rate of the feeding air stream 23. This is in particular important, where the total flow rate is relatively low in consideration of the preferably high flow resistance and resulting lower mean flow velocity.

According to another aspect, the mean velocity is preferably at least 50 m/s even at a comparatively low total flow rate of 39 l/min or less. This mean flow velocity is in particular at least 55 m/s, preferably about 60 m/s or more. This "mean flow velocity" means the flow velocity in the mixing zone 22 or at the end of the feeding path 21 (here at the outlet of channel 28).

The preferred high mean flow velocity results in an improved deagglomeration of the powder 10 (inhalation formulation). In particular, the mean flow velocity is significantly higher than in previous constructions.

It has to be noted that FIG. 3 shows only very schematically, in particular not in scale, a potential construction. Other constructional solutions are possible as a wall.

The channel 28 may taper towards its outlet end as shown in FIG. 3. However, the channel 28 may also have essentially a constant inner diameter or cross sectional area or taper in the opposite direction.

The channel 28 is preferably cylindrical or circular in cross section. However, the channel 28 may also be oval. The same applies for the outlet tube 18 and/or mouthpiece 8.

Preferably, the outlets of the feeding path 20 (channel 28) and of the bypass path 21 (grooves 29) are located as close as possible. In particular, the intermediate or annular wall 30 is formed as thin as possible towards the mixing zone 22 which follow the outlets of the feeding and/or bypass path 20, 21.

In the present embodiment, the bypass path 21 surrounds radially with its outlet(s) the preferably centrally arranged feeding path 20/channel 28. However, over constructional solutions are possible.

In the present embodiment, multiple—e.g. 4 or 6—channels or grooves 29 form the bypass path 21. However, other constructional solutions are possible. For example, the bypass path 21 could be formed by a channel which is essentially annual or oval in cross section or at its outlet end or which forms two half-ring outlets or the like.

Further, it has to be noted that other piercing elements 25, 26 and/or arrangements of the piercing elements 25, 26 can be used.

Preferably, the inhaler 1 is portable, works only mechanically and/or is handheld.

Preferably, the terms "blister strip" and "blister pockets" have to be understood in a very broad sense to cover also other kinds of storage means with receptacles or even bulk storages for the formulation.

LIST OF REFERENCE NUMBERS 1 inhaler
2 blister strip
3 blister pocket
4 reservoir
5 conveyor
5a onward movement
6 opening and/or removal position
7 piercing member
8 mouthpiece
9 air stream
10 powder
11 aerosol cloud
12 actuator
12a housing
13 receiving apparatus
14 conveying wheel
15 mouthpiece cover
16 cover axis
17 insert
18 outlet tube
19 air opening
20 feeding path
21 bypass path
22 mixing zone
23 feeding air stream
24 bypass air stream
25 first piercing element
26 second piercing element
27 lid
28 channel
29 groove
30 wall

The invention claimed is:

1. Inhaler for delivery of an inhalation formulation from a band-shaped blister strip with a plurality of blister pockets containing the inhalation formulation in doses, comprising:
   a conveyor for stepwise onward movement of the blister strip,
   a piercing member and a piercing element to puncture a lid of an aligned blister pocket, and
   a mouthpiece,
   the inhaler being designed such that by breathing in during inhalation an air stream of ambient air can be sucked in order to discharge the respective dose from an opened blister pocket and to deliver it with the ambient air as an aerosol cloud,
   wherein the mouthpiece comprises an insert to increase a flow resistance to at least 75,000 $Pa^{1/2}s/m^3$, the insert being located adjacent to the piercing member of the inhaler.

2. Inhaler according to claim 1, wherein the inhaler has a flow resistance of at least 90,000 $Pa^{1/2}s/m^3$.

3. Inhaler according to claim 1, the insert is held form-fit within the mouthpiece or an outlet tube thereof.

4. Inhaler according to claim 1, wherein the insert forms or holds the piercing member.

* * * * *

UNITED STATES PATENT AND TRADEMARK OFFICE
CERTIFICATE OF CORRECTION

| | | |
|---|---|---|
| PATENT NO. | : 8,511,300 B2 | Page 1 of 1 |
| APPLICATION NO. | : 12/864386 | |
| DATED | : August 20, 2013 | |
| INVENTOR(S) | : Herbert Wachtel | |

It is certified that error appears in the above-identified patent and that said Letters Patent is hereby corrected as shown below:

ON THE TITLE PAGE: ITEM 73 ADD

BOEHRINGER INGELHEIM INTERNATIONAL GmbH, INGELHEIM am RHEIN, DE

Signed and Sealed this
Fourth Day of March, 2014

Michelle K. Lee
*Deputy Director of the United States Patent and Trademark Office*